United States Patent
Chua, Jr.

(10) Patent No.: US 10,456,442 B2
(45) Date of Patent: Oct. 29, 2019

(54) FGF RECEPTOR LIGANDS FOR TREATING DIABETES AND OBESITY

(71) Applicant: ALBERT EINSTEIN COLLEGE OF MEDICINE, Bronx, NY (US)

(72) Inventor: Streamson Chua, Jr., Dobbs Ferry, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/579,988

(22) PCT Filed: May 10, 2016

(86) PCT No.: PCT/US2016/031575
§ 371 (c)(1),
(2) Date: Dec. 6, 2017

(87) PCT Pub. No.: WO2016/204884
PCT Pub. Date: Dec. 22, 2016

(65) Prior Publication Data
US 2018/0169181 A1 Jun. 21, 2018

Related U.S. Application Data

(60) Provisional application No. 62/181,413, filed on Jun. 18, 2015.

(51) Int. Cl.
*A61K 9/00* (2006.01)
*A61P 3/04* (2006.01)
*A61P 3/10* (2006.01)
*A61K 38/10* (2006.01)

(52) U.S. Cl.
CPC .............. *A61K 38/10* (2013.01); *A61K 9/0043* (2013.01); *A61P 3/04* (2018.01); *A61P 3/10* (2018.01)

(58) Field of Classification Search
CPC ......... A61K 38/10; A61K 9/0043; A61P 3/10; A61P 3/04
See application file for complete search history.

(56) References Cited

U.S. PATENT DOCUMENTS

2005/0026832 A1 2/2005 Adams et al.
2005/0026838 A1* 2/2005 Greene ................ A01K 67/027
435/69.1
2007/0015271 A1 1/2007 Rosen et al.

FOREIGN PATENT DOCUMENTS

WO 2015121457 A1 8/2015

OTHER PUBLICATIONS

French et al, Targeting FGFR4 Inhibits Hepatocellular Carcinoma in Preclinical Mouse Models, PLoS ONE, 2012, 7, e36713, pp. 1-12.*
Fuhrmann et al, Fibroblast Growth Factor Receptor 4 (FGFR4) Is Expressed in Adult Rat and Human Retinal Photoreceptors and Neurons, Journal of Molecular Neuroscience, 1999, 13, pp. 187-197.*
PCT International Search Report and Written Opinion, dated Aug. 26, 2016 in connection with PCT International Application No. PCT/US2016/031575, 9 pages.
Goetz R et al., entitled "Klotho Coreceptors Inhibit Signaling by Paracrine Fibroblast Growth Factor 8 Subfamily Ligands," Molecular and Cellular Biology, Mar. 26, 2012, vol. 32, pp. 1944-1954.
Hébert J M, entitled FGFs: neurodevelopment's Jack-of-all-trades—how do the do it? Front Neurosci, Dec. 5, 2011, vol. 5, pp. 1-10.
Kharitonenkov A et al., entitled "FGF-21 as a novel metabolic regulator," J Clin Invest., May 2, 2005, vol. 115, pp. 1627-1635.

* cited by examiner

*Primary Examiner* — Karlheinz R. Skowronek
*Assistant Examiner* — Li N Komatsu
(74) *Attorney, Agent, or Firm* — Fox Rothschild LLP (57) ABSTRACT

Methods for treating diabetes or obesity are provided comprising administering to the subject an amount of an agent that binds a central nervous system FGF receptor homodimer.

7 Claims, 4 Drawing Sheets
Specification includes a Sequence Listing.

```
FGF8a   TQR------------HVREQSLV
FGF8b   SQQ-VTVQSSPNFTQHVREQSLV
FGF17a  QTQ------------YVRDQGAM
FGF17b  QTQ-GENHPSPNFNQYVRDQGAM
FGF18   QVQVLAAEENVDFRIHVENQTRA
```

Fig. 4

FGF RECEPTOR LIGANDS FOR TREATING DIABETES AND OBESITY

CROSS-REFERENCE TO RELATED APPLICATIONS

This application is a U.S. national stage entry under 35 U.S.C. § 371 of PCT International Patent Application No. PCT/US2016/031575, filed May 10, 2016, which claims benefit of U.S. Provisional Application No. 62/181,413, filed Jun. 18, 2015, the contents of each of which are incorporated herein by reference into the subject application.

BACKGROUND OF THE INVENTION

All publications, patents, patent application publications and books referred to herein, including those referred to by number in brackets and recited at the end of the specification, are each hereby incorporated by reference in their entirety into the subject application to more fully describe the art to which the subject invention pertains.

Obesity and diabetes are disorders which have reached epidemic proportions worldwide. It is estimated that at least 25% of the adult US population is overweight, while type 2 diabetes affects about 9.3% of the US population. Effective therapies for weight control are limited in efficacy. Diabetes medications meet with limited patient compliance. Thus, there is a very large demand for effective treatments readily accepted by the patient population.

Herein is disclosed a method for treating diabetes or obesity using an agent that binds a central nervous system FGF receptor homodimer.

SUMMARY OF THE INVENTION

A method of treating diabetes or obesity in a subject comprising administering to the subject an amount of an agent that binds a central nervous system FGF receptor homodimer effective to treat diabetes or obesity in a subject.

A method of improving glucose tolerance in a subject comprising administering to the subject an amount of an agent that binds a central nervous system FGF receptor homodimer effective to improve glucose tolerance in a subject.

A method of treating a prediabetes hyperglycemic episode in a subject comprising administering to the subject an amount of an agent that binds a central nervous system FGF receptor homodimer effective to treat a prediabetes hyperglycemic episode in a subject.

Also provided is a method of treating diabetes or obesity in a subject comprising administering to the subject an amount of an agent comprising a peptide having the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1) effective to treat diabetes or obesity in a subject.

Also provided is a method of treating a prediabetes hyperglycemic episode in a subject comprising administering to the subject an amount of an agent comprising a peptide having the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1) effective to treat a prediabetes hyperglycemic episode in a subject.

BRIEF DESCRIPTION OF THE DRAWINGS

FIG. 2A-2E. ERK1/2 signaling involved in FGF19-glucose metabolism regulation. (2A) GTT with 2 g/kg of glucose (intraperitoneal injection) was performed after 6 hours of fast on HFD mouse males treated with icy injection of vehicle or U0126 (2B) GTT (2 g/kg) was performed after 6 hours of fast on HFD males treated icy with vehicle+FGF19 or U0126+FGF19. Mice were treated twice with FGF19 (starting 16 hours after fasting and 6.5 hours apart) and tissues were collected 90 minutes after the last ip injection (2C) Analysis of co-localization between Npy-hrGFP positive neurons (lighter gray) and p-ERK1/2 positive cells (darker gray) in 24 h fasted ob/ob Npy-hrGFP mice following intraperitoneal injections of FGF19. (2D) Quantification of Npy-hrGFP positive neurons that colocalize with pERK1/2 staining in ARC (Bregma −1.7 to −1.9 mm) of ob/ob Npy-hrGFP mice (10 sections from 3 mice were examined in each group). (2E) Representative sections showing absence of co-localization between Pomc-eGFP positive neurons (lighter gray) and p-ERK1/2 positive cells (darker gray) in 24 h fasted ob/ob Pomc-eGFP mice following intraperitoneal injections of FGF19. *$P<0.05$, ***$P<0.005$.

FIG. 3. Reduced fat mass and improved glucose tolerance due to absence of FGFR2 in hypothalamic AGRP/NPY neurons. Male mice (controls and AGRP:Fgfr2−/−) were placed on a high fat diet at 4 weeks of age (n=4-5 per group) and analyzed at 16 weeks of age. Body compositions (top panel) were determined by nuclear magnetic resonance spectroscopy with only fat mass showing a significant difference. Glucose tolerance tests (middle panel) were performed after an overnight fast with a glucose load of 1mg/g body weight. Insulin tolerance tests (bottom panel) were done in the post-prandial state. Data are presented as means and standard deviations. An asterisk signifies a statistically significant difference ($p<0.05$; t-test).

DETAILED DESCRIPTION OF THE INVENTION

A critical site of action for the metabolic effects of FGF19 is identified herein to be the hypothalamus. Based on data derived from delivery of bile acids and FGF19 in combination with the impact of ablating expression of FGF receptors within the hypothalamus, a framework is provided wherein competition between FGF receptors in homodimers and heterodimers (with Klotho co-receptors) can be manipulated to improve metabolic status. Various FGF-derived peptides have effects on body mass, body composition and glucose metabolism. Agents are disclosed, including peptides, that will lower body fat and improve glucose tolerance.

A method of treating diabetes or obesity in a subject comprising administering to the subject an amount of an agent that binds a central nervous system FGF receptor homodimer effective to treat diabetes or obesity in a subject.

A method of improving glucose tolerance in a subject comprising administering to the subject an amount of an agent that binds a central nervous system FGF receptor homodimer effective to improve glucose tolerance in a subject.

A method of treating a prediabetes hyperglycemic episode in a subject comprising administering to the subject an amount of an agent that binds a central nervous system FGF receptor homodimer effective to treat a prediabetes hyperglycemic episode in a subject.

In an embodiment of the methods, the agent does not bind an central nervous system FGF receptor-Klotho heterodimer, and/or the agent prevents a Klotho binding to an FGF receptor to which the agent is bound.

In an embodiment of the methods, the agent comprises a peptide comprising a phenylalanine residue.

Also provided is a method of treating diabetes or obesity in a subject comprising administering to the subject an amount of an agent comprising a peptide having the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1) effective to treat diabetes or obesity in a subject. In an embodiment, the agent comprsing the peptide does not comprise any further N-terminal amino acid(s) linked to X1-X2-F-X3-X4-X5-V-X6-X7-Q-X8-X9-X10. In an embodiment, the agent comprsing the peptide does not comprise any further C-terminal amino acid(s) linked to X1-X2-F-X3-X4-X5-V-X6-X7-Q-X8-X9-X10. In an embodiment, the agent comprsing the peptide does not comprise any further N-terminal amino acid(s) or C-terminal amino acid(s) linked to X1-X2-F-X3-X4-X5-V-X6-X7-Q-X8-X9-X10.

Also provided is a method of treating a prediabetes hyperglycemic episode in a subject comprising administering to the subject an amount of an agent comprising a peptide having the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1) effective to treat a prediabetes hyperglycemic episode in a subject. In an embodiment, the agent comprsing the peptide does not comprise any further N-terminal amino acid(s) linked to X1-X2-F-X3-X4-X5-V-X6-X7-Q-X8-X9-X10. In an embodiment, the agent comprsing the peptide does not comprise any further C-terminal amino acid(s) linked to X1-X2-F-X3-X4-X5-V-X6-X7-Q-X8-X9-X10. In an embodiment, the agent comprsing the peptide does not comprise any further N-terminal amino acid(s) or C-terminal amino acid(s) linked to X1-X2-F-X3-X4-X5-V-X6-X7-Q-X8-X9-X10.

In an embodiment of the methods, the agent comprises a peptide having the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1).

In an embodiment of the methods, X1 is P, X2 is N, X4 is Q, and X6 is R (SEQ ID NO:2).

In an embodiment of the methods, X3 is T or N, X7 is E or D, X8 is S or G, X9 is L or A, and X10 is V or M (SEQ ID NO:3).

In an embodiment of the methods, the agent comprises PNFTQHVREQSLV (SEQ ID NO:4). In an embodiment the agent does not comprise SPNFTQHVREQSLV. (SEQ ID NO:12)

In an embodiment of the methods, the agent comprises PNFNQYVRDQGAM (SEQ ID NO:5). In an embodiment the agent does not comprise SPNFNQYVRDQGAM (SEQ ID NO:13)

In an embodiment of the methods, the agent comprises VDFRIHVENQTRA (SEQ ID NO:6). In an embodiment the agent does not comprise NVDFRIHVENQTRA (SEQ ID NO:14).

In an embodiment of the methods, the agent comprises a peptide X1-X2-F-X3-X4-X5-V-X6-X7-Q-X8-X9-X10 having 90% or more sequence identity to (SEQ ID NO:4). In an embodiment of the methods, the agent comprises a peptide X1-X2-F-X3-X4-X5-V-X6-X7-Q-X8-X9-X10 having 90% or more sequence identity to (SEQ ID NO:5). In an embodiment of the methods, the agent comprises a peptide X1-X2-F-X3-X4-X5-V-X6-X7-Q-X8-X9-X10 having 90% or more sequence identity to (SEQ ID NO:6). In an embodiment of the methods, the agent is 13 amino acids in length.

In an embodiment of the methods, the agent comprises a peptide X1-X2-F-X3-X4-X5-V-X6-X7-Q-X8-X9-X10 having 95% or more sequence identity to (SEQ ID NO:4). In an embodiment of the methods, the agent comprises a peptide X1-X2-F-X3-X4-X5-V-X6-X7-Q-X8-X9-X10 having 95% or more sequence identity to (SEQ ID NO:5). In an embodiment of the methods, the agent comprises a peptide X1-X2-F-X3-X4-X5-V-X6-X7-Q-X8-X9-X10 having 95% or more sequence identity to (SEQ ID NO:6). In an embodiment of the methods, the agent is 13 amino acids in length.

In an embodiment of the methods, the agent comprises a peptide linked to a molecular entity which increases plasma half-life of the peptide. In an embodiment, the molecular entity which increases plasma half-life of the peptide is not itself a peptide. In an embodiment of the methods, the molecular entity is a polyethylene glycol (PEG).

In an embodiment, the molecular entity which increases plasma half-life of the peptide is an albumin-binding peptide attached to the peptide having the sequence X1-X2-F-X3-X4-X5-V-X6-X7-Q-X8-X9-X10 via a linker or directly. In an embodiment, the molecular entity which increases plasma half-life of the peptide is an albumin-binding antibody fragment conjugated to the peptide having the sequence X1-X2-F-X3-X4-X5-V-X6-X7-Q-X8-X9-X10 via a linker or directly.

In an embodiment of the methods, the peptide is acylated. In an embodiment of the methods, the peptide is not acylated.

In an embodiment of the methods, the agent is administered in a pH-buffered solution. In an embodiment of the methods, the agent is administered in a sterile solution. In an embodiment of the methods, the agent is administered in a sterile pH-buffered solution. In an embodiment of the methods, the pH-buffered solution comprises an artificial pH-buffer.

In an embodiment of the methods, the agent is administered in a manner such that it can enter the central nervous system of the subject.

In an embodiment of the methods, the agent is administered systemically to the subject.

In an embodiment of the methods, the agent is administered parenterally to the subject.

In an embodiment of the methods, the agent is administered to nasal epithelia of the subject.

In an embodiment of the methods, the agent is administered by injection into the subject. In an embodiment of the methods, the agent is administered by subcutaneous injection into the subject.

In an embodiment of the methods, the agent is administered directly to the central nervous system of the subject.

In an embodiment of the methods, the agent is administered weekly. In an embodiment of the methods, the agent is administered biweekly. In an embodiment of the methods, the agent is administered monthly. In an embodiment of the methods, the agent is administered daily.

In an embodiment of the methods, the agent is administered from an implanted device that delivers the agent from a reservoir. In an embodiment the reservoir is a dry reservoir. In an embodiment of the methods, the agent is administered from an implanted device that delivers the agent from a reservoir via an osmotic pump mechanism. In an embodiment of the methods, the agent is chronically administered from an implanted device that delivers the agent from a reservoir.

In an embodiment of the methods, the method is to treat diabetes. In an embodiment of the methods, the diabetes is type II diabetes (also called type 2 diabetes). In an embodiment of the methods, the method is to treat obesity. In an embodiment of the methods, the method treats prediabetes. In an embodiment of the methods, the method treats prediabetes hyperglycemia.

As used herein, "treating" a diabetes means that one or more symptoms of the disease, such as the diabetes itself, or a resultant symptom of the diabetes such as blindness, heart damage, lower limb ischemia or other parameters by which the disease is characterized, are reduced, ameliorated, inhibited, placed in a state of remission, or maintained in a state of remission. In an embodiment, the method inhibits further development of the diabetes. In an embodiment, the method inhibits further development of a pathology that results from the diabetes.

The invention also provides a method of treating a prediabetes transient hyperglycemic episode. As used herein, "treating" a prediabetes transient hyperglycemic episode means that one or more symptoms of the disease, such as damage resulting from hyperglycemia (e.g. tissue damage), or other parameters by which the disease is characterized, are reduced, ameliorated, inhibited, or maintained in a state of prediabetes. In an embodiment, the method inhibits further development of the prediabetes into diabetes. In an embodiment, the method inhibits further development of a pathology that results from the prediabetes hyperglycemia.

In an embodiment, a prediabetes transient hyperglycemic episode is considered a transient hyperglycemia of blood sugar >180 mg/dL to >240 mg/dL. In an embodiment, a prediabetes transient hyperglycemic episode is considered a transient hyperglycemia of blood sugar >200 mg/dL.

As used herein, "treating" obesity in a subject who has obesity means to stabilize, reduce, ameliorate or eliminate a sign or symptom of obesity in the subject. In an embodiment, obesity as used herein is characterized by the subject having a body mass index of 30.0 or greater (and thus includes the states of significant obesity, morbid obesity, super obesity, and super morbid obesity). In regard to gender, women with over 30% body fat are considered obese, and men with over 25% body fat are generally considered obese. The methods of treating obesity as disclosed herein are also applicable to treating an overweight state in a subject, defined as a body mass index of the subject of from 25.0 to 29.9, so as to stabilize, reduce, ameliorate or eliminate a sign or symptom of the overweight state in the subject.

In an embodiment, the agent that binds a central nervous system FGF receptor homodimer effective to treat diabetes or obesity in a subject inhibits or antagonizes the FGF receptor homodimer.

Klotho is a type-I membrane protein (e.g. RefSeq. NP_004786) encoded in humans by the KL gene (e.g. NM_004795). In an embodiment of the methods, the Klotho is a human Klotho.

In an embodiment of the methods, the FGF receptor is a human FGF receptor (human FGFR). In an embodiment of the methods, the FGF receptor is a type IIIc isoform. In an embodiment of the methods, the FGF receptor is a FGFR1. In an embodiment of the methods, the FGF receptor is a FGFR2.

There are 21 isoforms of FGFR1 (principally due to splicing) in humans. The UNIPARC identifiers for these 21 protein isoforms are (UniProtKB/Swiss-Prot) P11362-1 through P11362-21. Each of these is part of an individual embodiment of the invention where FGFR is recited. Similarly, there are 10 protein isoforms for FGFR2 with accession number P21802 (UniProtKB/Swiss-Prot). Each of these is part of an individual embodiment of the invention where FGFR is recited.

Both FGFR1 and FGFR2 bind FGF8 with high affinity, FGFR1 more so. The splice isoforms, which are also encompassed by the invention, are the IIIc forms of both receptors. The brain is highly enriched in the IIIc isoforms.

This invention will be better understood from the examples follow. However, one skilled in the art will readily appreciate that the specific methods and results discussed are merely illustrative of the invention as described more fully in the claims that follow thereafter.

EXAMPLE 1

Fibroblast growth factor (FGF) signaling has been implicated in the regulation of energy balance along with glucose and lipid homeostasis. Two of the three endocrine FGFs, FGF19 and FGF21, but not FGF23, have demonstrated capacities to prevent or ameliorate diet induced obesity, improve glucose homeostasis and reduce hepatosteatosis (1,2). While peripheral organs have been suggested as important targets of FGF effects, it has been demonstrated that FGF19 affects the central nervous system to reduce body weight and improve glucose control (3). Melanocortins are critical mediators of FGF19's effects. It was shown that FGF19 activated ERK1/2 in hypothalamic AGRP/NPY neurons, but FOS was reduced. Moreover, FGF19 prevented the induction of AGRP and NPY mRNA in mice fasted overnight. Interestingly, no effects of FGF19 were seen on POMC neurons. In its actions, FGF19 appears to be a partial leptin mimetic by activating signaling pathways in hypothalamic AGRP/NPY neurons that are downregulated in leptin resistant states.

Using genetic models of ablating FGF receptors within hypothalamic AGRP/NPY neurons it was predicted that ablation of FGFR1 and/or FGFR2 in hypothalamic AGRP/NPY neurons would result in obese and insulin resistant mice. However, studies of two genetic models, AGRP:Fgfr1−/− and AGRP:Fgfr2−/−, indicate that ablation of FGF receptor signaling prevents weight gain and improves glucose tolerance. These data indicate that both FGFR1 and FGFR2 have metabolic actions. One explanation is that these effects are due to compensatory effects as the genetic ablations occur during a period of high plasticity within the CNS. Alternatively, these data support the possibility of a second ligand (an alternative or alternative set of ligands) for hypothalamic FGFR1 and FGFR2, in addition to FGF19. These data could be explained by the ability of FGF receptors to form homodimers in response to conventional FGFs and FGFR-Klotho heterodimers to signal binding of endocrine FGFs.

FGFR1 and FGF8 constitute a receptor/ligand pair that exerts major effects on brain development (4). While total absence of FGFR1 and FGF8 are lethal, partial deficiencies in humans are associated with defective development of the olfactory bulb and gonadotrophin hormone releasing hormone (GnRH) neurons (5). Metabolic disturbances in patients with mutant FGFR1 or FGF8 have not been reported although major confounding effects of altered sex hormone production and altered pubertal development should be taken into account in interpreting the clinical presentations of such individuals. FGF8, along with FGF17 and FGF18 (FGF8 subfamily), are secreted proteins which are localized by their heparan sulfate binding regions to function as patterning and guiding signals for neurons. FGF8 binds directly to a groove conserved between FGFR1, FGFR2 and FGFR3 (6). This groove also binds Klotho and beta Klotho, co-receptors for FGF receptors that avidly bind FGF19 and FGF21. Thus, there is competitive binding between FGF8 and Klotho to FGFRs, providing a structural basis for antagonism between FGF8 and FGF19. Moreover, FGF8 has multiple splice isoforms with the main forms being FGF8a and FGF8b that apparently have antagonistic actions (7). This model is relevant only to FGF receptors of the IIIc isoforms which are principally expressed in the brain. Removal of the heparan sulfate binding domain may prolong retention time although biological activity is likely to be reduced (but not eliminated). Also, FGF8 is the prototype of a gene family that includes FGF17 and FGF18. Thus, there are multiple means of manipulating FGF8 signaling due to the intrinsic complexity of its biology.

Figure 1:
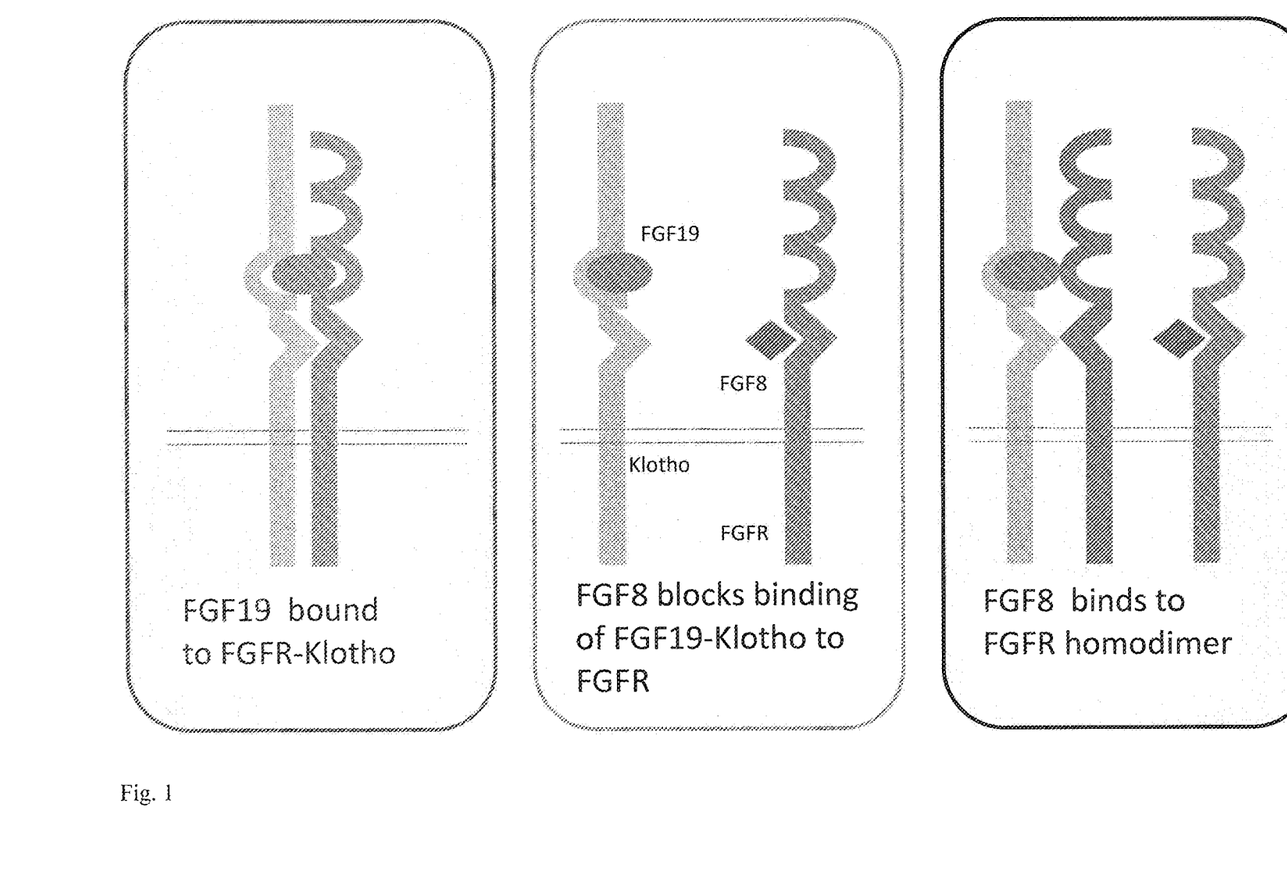
FIG. 1. A model for antagonism between FGF8 and FGF19/15 at FGF receptors. FGF8 is represented by a diamond and binds to homodimeric FGF receptors (dark-colored membrane spanning receptor) directly. FGF19/15 is represented by an oval and binds to klotho (light-colored membrane spanning receptor) directly which then forms a heteromeric complex with FGF receptors.
Figure 2A:
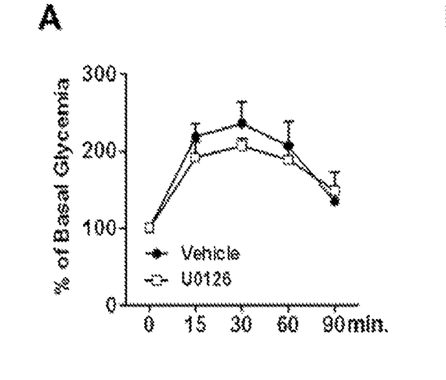
Figure 2B:
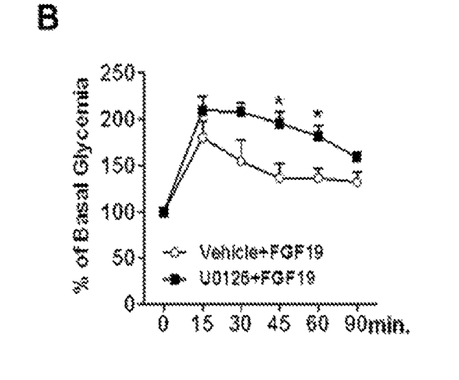

Central FGF19 effects on glucose metabolism rely on functional ERK1/2 signaling: It was previously shown that FGF19, injected centrally and peripherally, could improve glucose handling in obese mice (ob/ob) and high fat fed mice (3). It was assessed whether increased ERK1/2 activation could mediate the glucose lowering effect of FGF19. To that aim, the inhibitor U0126 was used on HFD-fed animals. Importantly, it was first determined that a dose of 5 μg of U0126 infused in the 3rd ventricle of HFD-fed males did not impact on glucose clearance during a GTT, to exclude any effect of U0126 itself on glucose metabolism (FIG. 2). Then, glucose tolerance was compared between HFD-fed mice that were pre-treated with vehicle or with U0126 thirty minutes before icy injection of FGF19. It was found that the pharmacological blockade of hypothalamic phosphorylation of ERK1/2 with U0126, blocked the glucose lowering effect of FGF19.

Figure 2C:
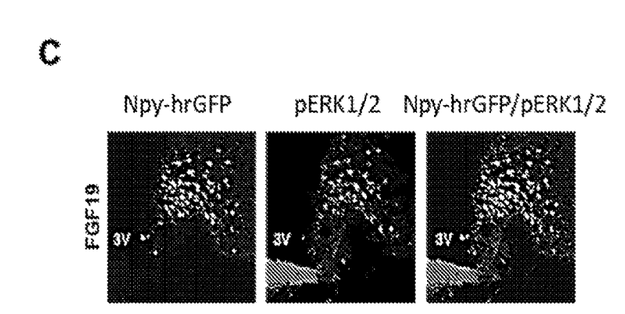
Figure 2D:
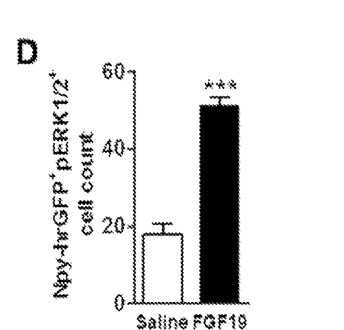
Figure 2E:
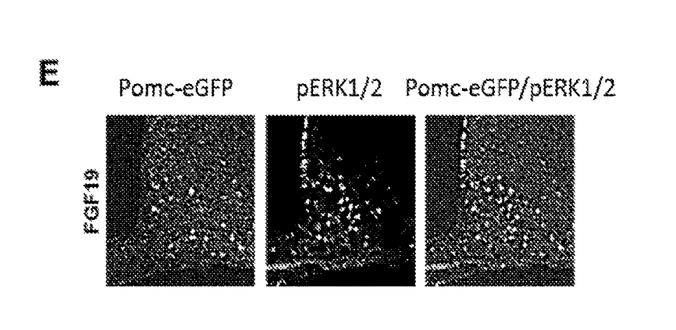

The neuronal population targeted by FGF19 was investigated. 24 h fasted Npy-hrGFP transgenic mice deficient in leptin (Npy-hrGFP ob/ob), in which AGRP/NPY neurons in ARC appear GFP+, were injected intraperitoneally with FGF19 and the colocalization between phospho-ERK1/2 and Npy-GFP was analyzed in ARC. Interestingly, it was found that FGF19-induced pERK1/2 staining colocalized with NPY-GFP+ neurons. A similar experiment performed in Pomc-eGFP ob/ob mice (POMC neurons appear GFP positive) showed that Pomc-eGFP positive neurons do not colocalize with pERK1/2 staining in ARC. Overall, the data support that central FGF19 improved glucose metabolism required activation of ERK1/2 signaling and that AGRP/NPY neurons are a likely mediator of FGF19 action.

Figure 3:
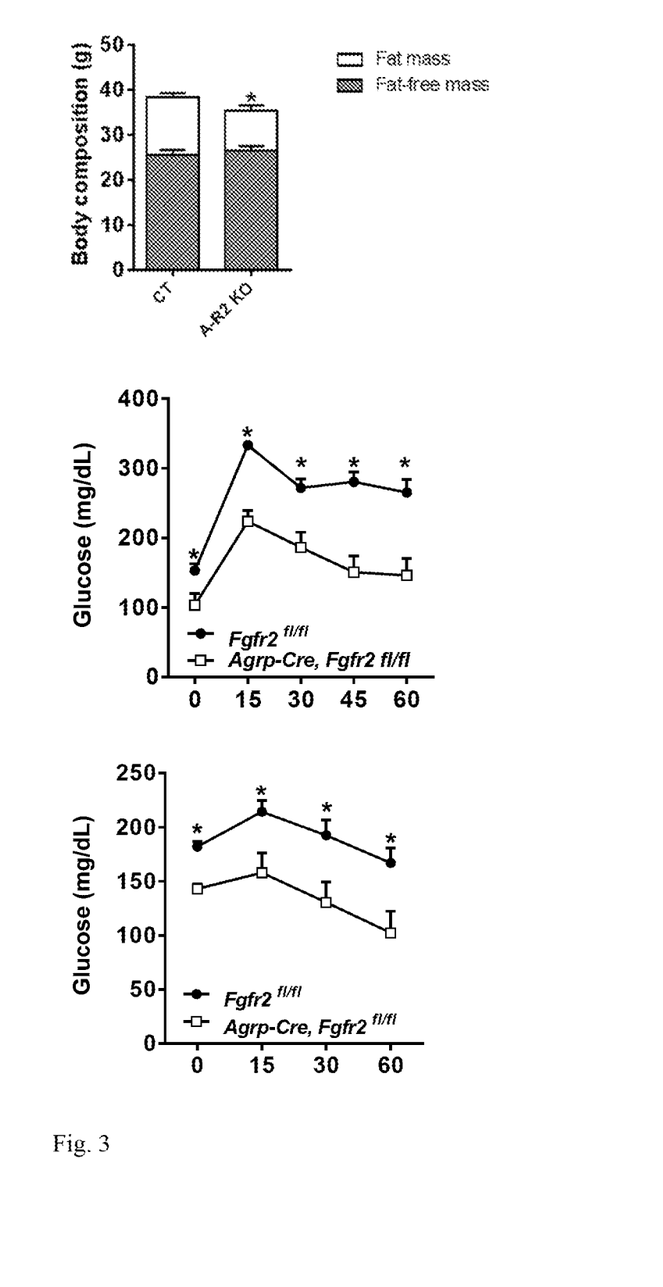

Loss of FGFR2 in AGRP/NPY neurons improves metabolic status: Data from mice (AGRP:Fgfr2−/−; genotype Fgfr2-flox/flox Agrp-CRE) shows expression of Fgfr2 is specifically ablated in hypothalamic AGRP neurons. Similar data were obtained from AGRP:Fgfr1 mice (data not shown) although the effects were observed on standard mouse chow and accentuated on high fat chow. After 3 months on a high fat diet, lower weight gain was observed in AGRP:Fgfr2 male mice compared to controls (Fgfr2-flox/flox). Glucose tolerance and insulin sensitivity were also improved in mice without FGFR2 in AGRP neurons. Interestingly, the Kd of FGFR2 for FGF8b (6) is ~twice that of FGFR1, providing a mechanism for the reduced efficacy of the FGFR2 ablation to impart DIO-resistance, relative to FGFR1 ablation. These data indicate that FGFR2 signaling in AGRP/NPY neurons are important for appropriate glucose homeostasis although the a priori prediction would have pointed to a worsened metabolic state in the absence of FGFR2. These conflicting data are reconciled in the model suggested in the previously presented model of antagonism between FGF ligands at FGF receptor homodimers and heterodimers.

Defining the effect of altering FGF receptor signaling in hypothalamic AGRP/NPY neurons after conditional expression of FGFR1 dominant negative and constitutive active lentivirus: Lentiviral constructs were developed for conditional expression of FGFR1 constructs that are dominant negative (FGFR1 wherein the entire intracytoplasmic tyrosine kinase domain is replaced by mCHERRY (8,9)) and constitutive active (fusion of Myc and the FGFR1 kinase domain bearing a point mutation [Lys656Glu] that confers high intrinsic kinase activity (10) to activate SHP2, PLC-gamma, MAPK, PI3K and STAT3). These lentiviral expression vectors are delivered bilaterally to the mediobasal hypothalamus of AGRP-CRE mice to activate expression of the FGFR1 constructs in AGRP/NPY neurons due to CRE mediated excision of a floxed transcriptional blocker cassette upstream on the coding sequence for FGFR1. Mice are placed on a high fat diet for up to 12 weeks. Subsequently, body weight gain and glucose tolerance along with insulin sensitivity is determined.

Structures of FGFR1 lentivirus constructs:
Myr—myristoylaton signal from v-src; CMV-cytomegalovirus promoter; mCherry—red shifted GFP. The virus has been tested by icy injection into Agrp-IRES-CRE mice and mCherry fluorescence observed, indicating successful CRE mediated expression of the FGFR1-mCherry fusion gene.

General construction of conditional FGFR1 within a lentivirus vector:
CMV promoter—loxP-polyA signal/transcriptional pause-loxP-FGFR1 Dominant negative—do-FGFR1 (SP-signal peptide; Ig-immunoglobulin like domain; TM-transmembrane domain):
CMV promoter—loxP-polyA/transcriptional pause-loxP-SP-Ig1-Ig2-Ig3-TM-mCherry
Constitutively active—ca-FGFR1 with K656E (activating) mutation:
myr—Kinase1-Kinase2-mCherry
K656E HEK 293 cells are transfected with the dnFGFR1-mCherry lentivirus. Cells are fixed and visualized by fluorescence of the cytoplasmically localized mCherry and nuclei stained with DAPI, a DNA-binding fluorochrome. Each blue DAPI-stained nucleus is enveloped within a red mCherry-labeled cytoplasmic shell. Cells are positively selected with puromycin as the lentivirus confers puromycin resistance.

Figure 4:
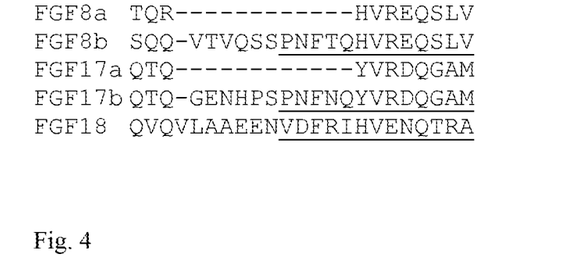
FIG. 4. Alignment of FGF8 family member isoforms highlighting the presence of a conserved phenylalanine among FGF8 family b isoforms. The alignment shows a phenylalanine (F) that differentiates between FGF8a and FGF8b biological activity. Structural analysis of FGF8b indicated that only the phenylalanine was in an ordered state when bound to FGFR1. The 13aa peptide used for probing glucose control in mice is underlined for each. (SEQ ID NO:7-11, top to bottom, respectively).

Defining the effects of FGF8b and FGF19 and their derived peptides on energy balance, body weight and glucose tolerance: Peptides derived from FGF8b, FGF17b and FGF18 (underlined in FIG. 4) are used for their capacity to improve glucose tolerance in high fat fed mice as well as ob/ob B6 mice. A mutant of FGF8b wherein the phenylalanine was mutated to an alanine (F61A) converted the peptide's activity spectrum to that of FGF8a (7), indicating the crucial nature of F61 residue for FGF8b activity. A mutated version of the FGF8b peptide with F61A is also employed to determine if it is as ineffective to improve glucose handling. Peptides are delivered by intraparenchymal injections into the medibasal hypothalamus. Insulin release and hepatic glucose production are also assessed as the mechanism(s) for the improved glucose parameters after FGF8b peptide administration. The ability of the peptide when injected systemically to affect glucose handling is also determined. High fat fed B6 mice are used for the systemic injections of peptide. Off target effects are unlikely due to the low affinity of non-IIIc FGF receptor isoforms (which are mainly expressed in the peripheral tissues) to bind FGF8b.

A peptide of 13 amino acids (PNFTQHVREQSLV) (SEQ ID NO:4) was synthesized based on the conserved sequences between the FGF8 and FGF17 b splice isoforms and the helical nature of this region of FGF8 based on a published crystal structure. This peptide was injected intraparenchymally into the mediobasal hypothalamus of 8 month old outbred mice. Having been fasted overnight, the mice were subjected to an oral glucose tolerance test (2 mg/g of glucose) using a crossover design to obtain a control condition. It was found that the FGF8b derived peptide improved glucose tolerance in mice when compared to the same mice after injection with artificial cerebrospinal fluid (aCSF). With aCSF, the median area under the curve for the 3 hour GTT was 43,747 mg-min/dL whereas it was 33,524 ng-min/dL with F8b13. Blood glucose concentrations were not different before the glucose load. These FGF derived peptide antagonists are useful as therapeutic agents in diabetes and obesity conditions.

REFERENCES

1. Tomlinson E, Fu L, John L, Hultgren B, Huang X, Renz M, Stephan J P, Tsai S P, Powell-Braxton L, French D, Stewart T A. Transgenic mice expressing human fibroblast growth factor-19 display increased metabolic rate and decreased adiposity. Endocrinology. 2002 May; 143(5):1741-7. PubMed PMID: 11956156.

2. Kharitonenkov A, Shiyanova T L, Koester A, Ford A M, Micanovic R, Galbreath E J, Sandusky G E, Hammond L J, Moyers J S, Owens R A, Gromada J, Brozinick J T, Hawkins E D, Wroblewski V J, Li D S, Mehrbod F, Jaskunas S R, Shanafelt A B. FGF-21 as a novel metabolic regulator. J Clin Invest. 2005 June; 115(6):1627-35. Epub 2005 May 2.PubMed PMID: 15902306; PubMed Central PMCID: PMC1088017.

3. Marcelin G, Jo Y H, Li X, Schwartz G J, Zhang Y, Dun N J, Lyu R M, Blouet C, Chang J K, Chua S Jr. Central action of FGF19 reduces hypothalamic AGRP/NPY neuron activity and improves glucose metabolism. MolMetab. 2013 Oct. 23; 3(1):19-28. doi: 10.1016/j.molmet.2013.10.002. eCollection 2014 February PubMed PMID: 24567901; PubMed Central PMCID: PMC3929918.

4. Hébert J M. FGFs: Neurodevelopment's Jack-of-all-Trades—How Do They Do it? Front Neurosci. 2011 Dec. 5; 5:133. doi: 10.3389/fnins.2011.00133. eCollection 2011. PubMed PMID: 22164131; PubMed Central PMCID: PMC3230033.

5. Valdes-Socin H, Rubio Almanza M, ToméFernández-Ladreda M, Debray F G, Bours V, Beckers A. Reproduction, smell, and neurodevelopmental disorders: genetic defects in different hypogonadotropic hypogonadal syndromes. Front Endocrinol (Lausanne). 2014 Jul. 9; 5:109. doi: 10.3389/fendo.2014.00109. eCollection 2014. Review. PubMed PMID: 25071724; PubMed Central PMCID: PMC4088923.

6. Goetz R, Ohnishi M, Ding X, Kurosu H, Wang L, Akiyoshi J, Ma J, Gai W, Sidis Y, Pitteloud N, Kuro-O M, Razzaque M S, Mohammadi M. Klotho coreceptors inhibit signaling by paracrine fibroblast growth factor 8 subfamily ligands. Mol Cell Biol. 2012 May; 32(10):1944-54. doi: 10.1128/MCB.06603-11. Epub 2012 Mar. 26. PubMed PMID: 22451487; PubMed Central PMCID: PMC3347405.

7. Guo Q, Li K, Sunmonu N A, Li J Y. Fgf8b-containing spliceforms, but not Fgf8a, are essential for Fgf8 function during development of the midbrain and cerebellum. Dev Biol. 2010 Feb. 15; 338(2):183-92. doi: 10.1016/j.ydbio.2009.11.034. Epub 2009 Dec. 5. PubMed PMID: 19968985; PubMed Central PMCID: PMC2815264.

8. Amaya E, Musci T J, Kirschner M W. Expression of a dominant negative mutant of the FGF receptor disrupts mesoderm formation in *Xenopus* embryos. Cell. 1991 Jul. 26; 66(2):257-70. PubMed PMID: 1649700.

9. Lee Y, Grill S, Sanchez A, Murphy-Ryan M, Poss K D. Fgf signaling instructs position-dependent growth rate during zebrafish fin regeneration. Development. 2005 December; 132(23):5173-83. Epub 2005 Oct. 26. PubMed PMID: 16251209.

10. Hart K C, Robertson S C, Kanemitsu M Y, Meyer A N, Tynan J A, Donoghue D J. Transformation and Stat activation by derivatives of FGFR1, FGFR3, and FGFR4. Oncogene. 2000 Jul. 6; 19(29):3309-20. PubMed PMID: 10918587.

What is claimed is:

1. A method of treating diabetes or obesity in a subject comprising administering to the subject a peptide consisting of the sequence X1-X2-F-X3-X4-X5-V-X6-X7-Q-X8-X9-X10, wherein F is a phenylalanine, V is a valine, Q is glutamine, X1 is the amino acid P or V, X2 is the amino acid N or D, X3 is the amino acid T, N or R, X4 is the amino acid Q or I, X5 is the amino acid H or Y, X6 is the amino acid R or E, X7 is the amino acid E, D or N, X8 is the amino acid S, G or T, X9 is the amino acid L, A or R, and X10 is the amino acid V, M or A (SEQ ID NO:1) in an amount effective to treat diabetes or obesity in the subject.

2. The method of claim 1, wherein X1 is P, X2 is N, X4 is Q, and X6 is R (SEQ ID NO:2).

3. The method of claim 2, wherein X3 is T or N, X7 is E or D, X8 is S or G, X9 is L or A, and X10 is V or M (SEQ ID NO:3).

4. The method of claim 1, wherein the peptide consists of the sequence PNFTQHVREQSLV (SEQ ID NO:4).

5. The method of claim 1, wherein the peptide consists of the sequence PNFNQYVRDQGAM (SEQ ID NO:5).

6. The method of claim 1, wherein the peptide consists of the sequence VDFRIHVENQTRA (SEQ ID NO:6).

7. The method of claim 1, wherein the diabetes is type II diabetes.

* * * * *

SEQUENCE LISTING

<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: peptide fragment based on human sequence
<220> FEATURE:
<221> NAME/KEY: MISC_FEATURE
<222> LOCATION: (1)..(1)
<223> OTHER INFORMATION: x = P or V
<220> FEATURE:
<221> NAME/KEY: MISC_FEATURE
<222> LOCATION: (2)..(2)
<223> OTHER INFORMATION: x = N or D
<220> FEATURE:
<221> NAME/KEY: MISC_FEATURE
<222> LOCATION: (4)..(4)
<223> OTHER INFORMATION: x = T,N or R
<220> FEATURE:
<221> NAME/KEY: MISC_FEATURE
<222> LOCATION: (5)..(5)
<223> OTHER INFORMATION: x = Q or I
<220> FEATURE:
<221> NAME/KEY: MISC_FEATURE
<222> LOCATION: (6)..(6)
<223> OTHER INFORMATION: x = H or Y
<220> FEATURE:
<221> NAME/KEY: MISC_FEATURE
<222> LOCATION: (8)..(8)
<223> OTHER INFORMATION: x = R or E
<220> FEATURE:
<221> NAME/KEY: MISC_FEATURE
<222> LOCATION: (9)..(9)
<223> OTHER INFORMATION: x = E, D or N
<220> FEATURE:
<221> NAME/KEY: MISC_FEATURE
<222> LOCATION: (11)..(11)
<223> OTHER INFORMATION: x = S, G or T
<220> FEATURE:
<221> NAME/KEY: MISC_FEATURE
<222> LOCATION: (12)..(12)
<223> OTHER INFORMATION: x = L,A or R
<220> FEATURE:
<221> NAME/KEY: MISC_FEATURE
<222> LOCATION: (13)..(13)
<223> OTHER INFORMATION: x = V,M or A

<400> SEQUENCE: 1

Xaa Xaa Phe Xaa Xaa Xaa Val Xaa Xaa Gln Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: peptide fragment based on human sequence
<220> FEATURE:
<221> NAME/KEY: MISC_FEATURE
<222> LOCATION: (4)..(4)
<223> OTHER INFORMATION: x = T, N or R
<220> FEATURE:
<221> NAME/KEY: MISC_FEATURE
<222> LOCATION: (6)..(6)
<223> OTHER INFORMATION: x = N or Y
<220> FEATURE:
<221> NAME/KEY: MISC_FEATURE
<222> LOCATION: (9)..(9)
<223> OTHER INFORMATION: x = E, D, or N
<220> FEATURE:
<221> NAME/KEY: MISC_FEATURE
<222> LOCATION: (11)..(11)
<223> OTHER INFORMATION: x = S, G, or T
<220> FEATURE:
<221> NAME/KEY: MISC_FEATURE
<222> LOCATION: (12)..(12)
<223> OTHER INFORMATION: x = L, A or R
<220> FEATURE:
<221> NAME/KEY: MISC_FEATURE
<222> LOCATION: (13)..(13)
<223> OTHER INFORMATION: x = V, M or A

<400> SEQUENCE: 2

Pro Asn Phe Xaa Gln Xaa Val Arg Xaa Gln Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: peptide fragment based on human sequence
<220> FEATURE:
<221> NAME/KEY: MISC_FEATURE
<222> LOCATION: (1)..(1)
<223> OTHER INFORMATION: x = P or V
<220> FEATURE:
<221> NAME/KEY: MISC_FEATURE
<222> LOCATION: (2)..(2)
<223> OTHER INFORMATION: x = N or D
<220> FEATURE:
<221> NAME/KEY: MISC_FEATURE
<222> LOCATION: (4)..(4)
<223> OTHER INFORMATION: x = T or N
<220> FEATURE:
<221> NAME/KEY: MISC_FEATURE
<222> LOCATION: (5)..(5)
<223> OTHER INFORMATION: x = Q or I
<220> FEATURE:
<221> NAME/KEY: MISC_FEATURE
<222> LOCATION: (6)..(6)
<223> OTHER INFORMATION: x = H or Y
<220> FEATURE:
<221> NAME/KEY: MISC_FEATURE
<222> LOCATION: (8)..(8)
<223> OTHER INFORMATION: x = R or E
<220> FEATURE:
<221> NAME/KEY: MISC_FEATURE
<222> LOCATION: (9)..(9)
<223> OTHER INFORMATION: x = E or D
<220> FEATURE:
<221> NAME/KEY: MISC_FEATURE
<222> LOCATION: (11)..(11)
<223> OTHER INFORMATION: x = S or G
<220> FEATURE:
<221> NAME/KEY: MISC_FEATURE
<222> LOCATION: (12)..(12)
<223> OTHER INFORMATION: x = L or A
<220> FEATURE:
<221> NAME/KEY: MISC_FEATURE
<222> LOCATION: (13)..(13)
<223> OTHER INFORMATION: x = V or M

<400> SEQUENCE: 3

Xaa Xaa Phe Xaa Xaa Xaa Val Xaa Xaa Gln Xaa Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: peptide fragment based on human sequence

<400> SEQUENCE: 4

Pro Asn Phe Thr Gln His Val Arg Glu Gln Ser Leu Val
1               5                   10

```
<210> SEQ ID NO 5
<211> LENGTH: 13
<212> TYPE: PRT
<213> ORGANISM: Artificial Sequence
<220> FEATURE:
<223> OTHER INFORMATION: peptide fragment based on human sequence

<400> SEQUENCE: 5

Pro Asn Phe Asn Gln Tyr Val Arg Asp Gln Gly Ala Met
1               5                   10

<210> SEQ ID NO 6
<211> LENGTH: 13
<212> TYPE: PRT
<213> ORGANISM: Artificial Sequence
<220> FEATURE:
<223> OTHER INFORMATION: peptide fragment based on human sequence

<400> SEQUENCE: 6

Val Asp Phe Arg Ile His Val Glu Asn Gln Thr Arg Ala
1               5                   10

<210> SEQ ID NO 7
<211> LENGTH: 11
<212> TYPE: PRT
<213> ORGANISM: Mus musculus

<400> SEQUENCE: 7

Thr Gln Arg His Val Arg Glu Gln Ser Leu Val
1               5                   10

<210> SEQ ID NO 8
<211> LENGTH: 22
<212> TYPE: PRT
<213> ORGANISM: Mus musculus

<400> SEQUENCE: 8

Ser Gln Gln Val Thr Val Gln Ser Ser Pro Asn Phe Thr Gln His Val
1               5                   10                  15

Arg Glu Gln Ser Leu Val
            20

<210> SEQ ID NO 9
<211> LENGTH: 11
<212> TYPE: PRT
<213> ORGANISM: Mus musculus

<400> SEQUENCE: 9

Gln Thr Gln Tyr Val Arg Asp Gln Gly Ala Met
1               5                   10

<210> SEQ ID NO 10
<211> LENGTH: 22
<212> TYPE: PRT
<213> ORGANISM: Mus musculus

<400> SEQUENCE: 10

Gln Thr Gln Gly Glu Asn His Pro Ser Pro Asn Phe Asn Gln Tyr Val
1               5                   10                  15

Arg Asp Gln Gly Ala Met
            20
```

```
<210> SEQ ID NO 11
<211> LENGTH: 23
<212> TYPE: PRT
<213> ORGANISM: Mus musculus

<400> SEQUENCE: 11

Gln Val Gln Val Leu Ala Ala Glu Glu Asn Val Asp Phe Arg Ile His
1               5                   10                  15

Val Glu Asn Gln Thr Arg Ala
            20

<210> SEQ ID NO 12
<211> LENGTH: 14
<212> TYPE: PRT
<213> ORGANISM: Artificial Sequence
<220> FEATURE:
<223> OTHER INFORMATION: peptide fragment based on human sequence

<400> SEQUENCE: 12

Ser Pro Asn Phe Thr Gln His Val Arg Glu Gln Ser Leu Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: peptide fragment based on human sequence

<400> SEQUENCE: 13

Ser Pro Asn Phe Asn Gln Tyr Val Arg Asp Gln Gly Ala Met
1               5                   10

<210> SEQ ID NO 14
<211> LENGTH: 14
<212> TYPE: PRT
<213> ORGANISM: Artificial Sequence
<220> FEATURE:
<223> OTHER INFORMATION: peptide fragment based on human sequence

<400> SEQUENCE: 14

Asn Val Asp Phe Arg Ile His Val Glu Asn Gln Thr Arg Ala
1               5                   10
```